United States Patent
Hirano et al.

(10) Patent No.: US 9,691,648 B2
(45) Date of Patent: Jun. 27, 2017

(54) PARTICLE SUPPLY DEVICE AND PARTICLE SUPPLY METHOD

(71) Applicant: Kabushiki Kaisha Toshiba, Minato-ku, Tokyo (JP)

(72) Inventors: Masaki Hirano, Mie (JP); Yuichi Kuroda, Mie (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 135 days.

(21) Appl. No.: 14/636,349

(22) Filed: Mar. 3, 2015

(65) Prior Publication Data

US 2016/0074821 A1    Mar. 17, 2016

(30) Foreign Application Priority Data

Sep. 11, 2014 (JP) ................................. 2014-185514

(51) Int. Cl.
| | |
|---|---|
| *G01N 1/22* | (2006.01) |
| *H01L 21/673* | (2006.01) |
| *G01N 1/40* | (2006.01) |
| *G01N 33/00* | (2006.01) |

(52) U.S. Cl.
CPC ...... *H01L 21/67389* (2013.01); *G01N 1/2214* (2013.01); *G01N 1/2226* (2013.01); *G01N 1/405* (2013.01); *G01N 33/0026* (2013.01); *G01N 2001/2223* (2013.01)

(58) Field of Classification Search
CPC .............................................. G01N 2001/2223
USPC .................... 73/31.03; 137/1, 561 R, 565.01
See application file for complete search history.

(56) References Cited

U.S. PATENT DOCUMENTS

| | | | | |
|---|---|---|---|---|
| 5,209,102 | A * | 5/1993 | Wang | G01N 15/06 73/28.01 |
| 5,665,902 | A * | 9/1997 | Wang | G01N 1/2226 73/28.01 |
| 5,949,001 | A * | 9/1999 | Willeke | G01N 15/0255 356/336 |
| 7,000,454 | B2 * | 2/2006 | Schneider | B08B 3/08 73/31.03 |
| 7,390,339 | B1 * | 6/2008 | Warrick | B01D 45/12 55/346 |

(Continued)

FOREIGN PATENT DOCUMENTS

| | | |
|---|---|---|
| JP | 7-312335 | 11/1995 |
| JP | 2003-303869 | 10/2003 |

(Continued)

OTHER PUBLICATIONS

Kazuhiro, Yamamato et al., Primary Particle Size Distribution Measurement of Nanomaterials by Using TEM, Microsc. Microanal. 20 (Suppl 3), Microscopy Society of America, 2014.*

(Continued)

*Primary Examiner* — Clayton E Laballe
*Assistant Examiner* — Kevin Butler
(74) *Attorney, Agent, or Firm* — Finnegan, Henderson, Farabow, Garrett & Dunner LLP (57) ABSTRACT

A particle supply device according to one embodiment includes a housing and a particle supplier. The housing seals a space between a substrate carry-out port provided in a FOUP and a substrate carry-in port provided at a load port of a substrate processing device. A particle supplier supplies particles to an inside of the housing.

10 Claims, 7 Drawing Sheets

(56) References Cited

U.S. PATENT DOCUMENTS

| | | | | |
|---|---|---|---|---|
| 7,647,810 | B2* | 1/2010 | Wei | F02D 41/1466 |
| | | | | 73/23.31 |
| 8,561,486 | B2* | 10/2013 | Novosselov | B01D 15/08 |
| | | | | 73/864.32 |
| 2006/0207971 | A1* | 9/2006 | Moriya | C23F 1/12 |
| | | | | 216/67 |
| 2010/0236406 | A1* | 9/2010 | Yamawaku | H01L 21/67017 |
| | | | | 95/58 |
| 2016/0074821 | A1* | 3/2016 | Hirano | H01L 21/67389 |
| | | | | 137/1 |

FOREIGN PATENT DOCUMENTS

| | | | | |
|---|---|---|---|---|
| JP | 2003303869 | * | 10/2003 | B65G 49/07 |
| JP | 2006-228808 | | 8/2006 | |
| JP | 2010-161157 | | 7/2010 | |

OTHER PUBLICATIONS

A.Zschunke, Reference Materials in Analytical Chemistry A Guide for Selection and Use, Springer-Verlag Berlin, Feb. 2000, pp. 126-127.*

PCT/JP2014/063050, Written Opinion of the International Searching Authority, Aug. 19, 2014, 5 pages.*

* cited by examiner

FIG. 7

PARTICLE SUPPLY DEVICE AND PARTICLE SUPPLY METHOD

CROSS REFERENCE TO RELATED APPLICATION(S)

This application is based upon and claims the benefit of priority from the prior Japanese Patent Application No. 2014485514, filed on Sep. 11, 2014, the entire contents of which are incorporated herein by reference.

FIELD

Embodiments described herein relate generally to a particle supply device and a particle supply method.

BACKGROUND

Conventionally, a positional relationship between a FOUP (Front Opening Unified Pod) and a load port of an EFEM (Equipment Front End Module) is defined by a SEMI (Semiconductor Equipment and Materials International) standard. However, a gap is formed between the FOUP and the load port due to a dimension error in processing the FOUP. Then, when a lid of the FOUP is opened, outside air intrudes from this gap, and an inside of the FOUP may be contaminated by dust in the outside air. Since such contamination causes a defect of a substrate stored in the FOUP, a dust intrusion evaluation which evaluates how much dust intrudes into the FOUP when the lid of the FOUP opened is performed at the time of introducing a facility.

However, in the conventional dust intrusion evaluation, an environment around the FOUP cannot be controlled. Because of this, environmental conditions are different every time the evaluation is performed, and it is difficult to perform a highly reliable evaluation. Further, it is neither possible to perform the evaluation on a plurality of load ports under the same environmental conditions nor to perform the evaluation under the same environmental conditions as those in a clean room utilized by the FOUP.

DETAILED DESCRIPTION

Embodiments will now be explained with reference to the accompanying drawings. The present invention is not limited to the embodiments.

A particle supply device according to one embodiment includes a housing and a particle supplier. The housing seals a space between a substrate carry-out port provided in a FOUP and a substrate carry-in port provided at a load port of a substrate processing device. A particle supplier supplies particles to an inside of the housing.

Figure 1:
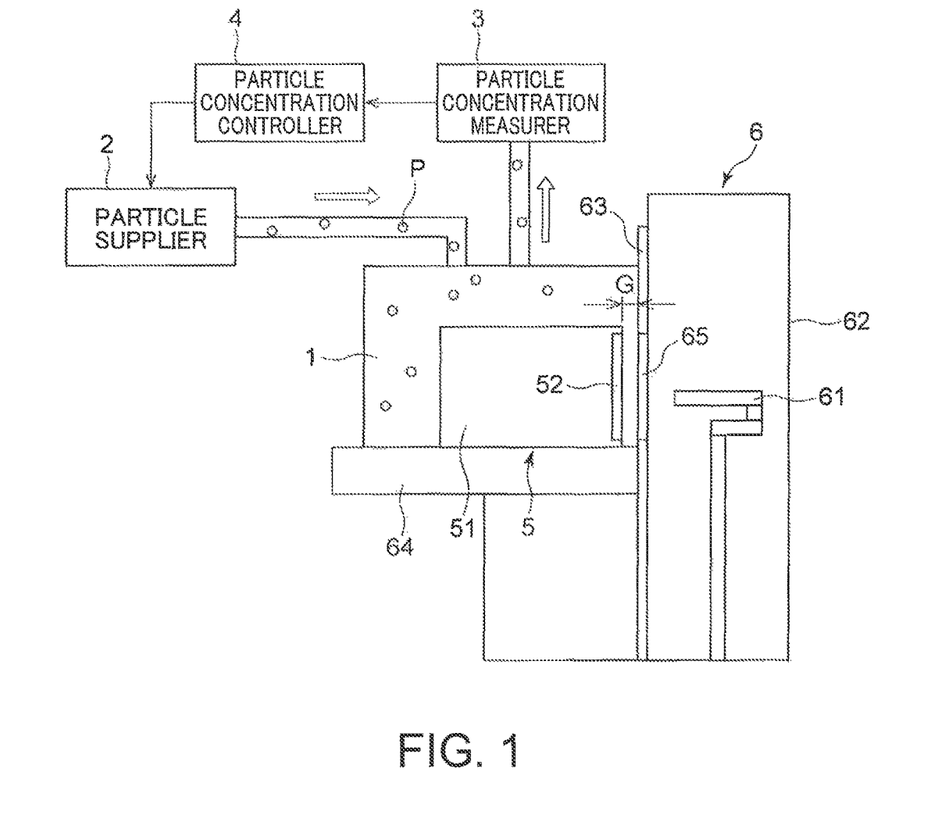
FIG. 1 is a schematic configuration diagram illustrating one example of a particle supply device according to a first embodiment.

First, a particle supply device according to a first embodiment will be explained with reference to FIG. 1. FIG. 1 is a schematic configuration diagram illustrating one example of the particle supply device according to the present embodiment. As illustrated in FIG. 1, this particle supply device includes a housing 1, a particle supplier 2, a particle concentration measurer 3, and a particle concentration controller 4. This particle supply device is a device for evaluating dust intrusion in a state in which a FOUP 5 is mounted on an EFEM 6. Here, the FOUP 5 and the EFEM 6 will be explained first.

The FOUP 5 is a substrate storage container which stores a substrate. The FOUP 5 includes a FOUP housing 51 and a lid 52. The FOUP housing 51 is formed so as to be capable of storing a plurality of substrates and has an opening part (substrate carry-out port) on a front surface. The substrate is carried in/out from this opening part. In FIG. 1, the front surface of the FOUP housing 51 is a right side surface of the FOUP housing 51. The lid 52 opens/closes the opening part on the front surface of the FOUP housing 51. When the lid 52 is closed, an inside of the FOUP housing 51 is sealed.

The EFEM 6 conveys the substrate stored in the FOUP 5 from the FOUP 5 to a substrate processing device in a mini environment system. The EFEM 6 includes a conveyance arm 61, a conveyance chamber 62, and a load port 63. The conveyance arm 61 conveys the substrate stored in the FOUP 5. The conveyance chamber 62 stores the conveyance arm 61. The substrate taken out from the FOUP 5 by the conveyance arm 61 is conveyed to the substrate processing device via the conveyance chamber 62. Because of this, an inside of the conveyance chamber 62 is maintained in a clean environment. Although not illustrated in FIG. 1, it is preferable that the EFEM 6 include a FFU (Fan Filter Unit) which cleans the inside of the conveyance chamber 62.

A load port 63 is an interface for delivering the substrate between the FOUP 5 and the EFEM 6. The load port 63 includes a table 64 and a lid 65. The FOUP 5 is placed on the table 64. The lid 65 opens/closes an opening part serving as a substrate entrance (substrate carry-in port). When the lid 65 is closed, the inside of the conveyance chamber 62 is sealed.

In a case where the substrate is conveyed from the FOUP 5 to the substrate processing device, first, the FOUP 5 is disposed at a predetermined position of the table 64 in such a manner that the lid 52 of the FOUP 5 and the lid 65 of the load port 63 face each other. At this time, a gap G is formed between the front surface of the FOUP 5 and the load port 63 due to a dimension error in processing the FOUP 5. A width of this gap G is usually within a range of tolerance of the FOUP 5.

Next, the lid 52 of the FOUP 5 and the lid 65 of the load port 63 are opened. Then, the substrate stored in the FOUP 5 is conveyed to the substrate processing device by the conveyance arm 61. With this configuration, the substrate is conveyed in the mini environment system.

As mentioned above, since the FOUP 5 is sealed by the lid 52, when the lid 52 is opened, a pressure therein becomes negative. When the pressure inside the FOUP 5 becomes negative, outside air flows in through the gap G and dust within the air intrudes into the FOUP housing 51. In a dust intrusion evaluation, an amount of dust intruded at this time is evaluated. The respective constitutions of the particle supply device will be explained below.

The housing 1 has an opening part on one surface and stores the FOUP 5 in such a manner that this opening part is located on a front surface side of the FOUP 5, When the dust intrusion evaluation is performed, the housing 1 is disposed in such a manner that this opening part comes in contact with the load port 63. With this configuration, a sealed space including the FOUP 5 is formed inside the housing 1. Hereinafter, the surface formed with the opening part will be referred to as "front surface" of the housing 1.

The particle supplier 2 supplies particles P to an inside of the housing 1. It is preferable that the particle P be a standard particle having a uniform particle diameter. The particle P is, for example, a PLS (Polystyrene latex) particle. However, the particle P is not limited to this. The particle diameter or the material of the particle P can be arbitrarily selected according to its use. In FIG. 1, the particle supplier 2 supplies the particles P to the housing 1 from an upper surface. However, the particle supplier 2 may supply the particles P to the housing 1 from a back surface or a side surface, or may supply the particles P to the housing 1 from a plurality of positions. A concrete configuration of the particle supplier 2 will be described below.

The particle concentration measurer 3 sucks air inside the housing 1. and measures particle concentration inside the housing 1.

The particle concentration means the number of particles per unit volume. For example, a PC (Particle Counter) can be used as the particle concentration measurer 3. In FIG, 1, the particle concentration measurer 3 sucks the air from the upper surface of the housing 1. However, the particle concentration measurer 3 may suck the air from the back surface or the side surface of the housing 1, or may suck the air from the plurality of positions of the housing 1.

The particle concentration controller 4 controls a supply amount of the particles P from the particle supplier 2 in such a manner that the particle concentration inside the housing 1 becomes a predetermined value. The particle concentration controller 4 acquires the particle concentration inside the housing 1 from the particle concentration measurer 3. In a case where the particle concentration is larger than the predetermined value, the particle concentration controller 4 decreases the supply amount of the particles P from the particle supplier 2. In a case where the particle concentration is smaller than the predetermined value, the particle concentration controller 4 increases the supply amount of the particles P from the particle supplier 2. With this configuration, the particle concentration inside the housing 1 becomes the predetermined value.

The aforementioned predetermined value can be set arbitrarily. Further, an upper limit value and a lower limit value of the particle concentration may be set as the predetermined values. In this case, the particle concentration controller 4 controls the particle supplier 2 in such a manner that the particle concentration inside the housing 1 is within a predetermined range from the upper limit value to the lower limit value. The predetermined value is, for example, an average value or a maximum value of particle concentrations in a space, such as a clean room, utilized by the FOUP 5. However, the predetermined value is not limited to this.

This particle concentration controller 4 is constituted of a computer device. The computer device includes a CPU, a main storage, and an external storage. When the CPU executes a particle concentration control program stored in the external storage, a function of the aforementioned particle concentration controller 4 is realized. The computer device constituting the particle concentration controller 4 may be provided independently, or may be provided integrally with a control device of the particle concentration measurer 3 or the particle supplier 2.

Figure 2:
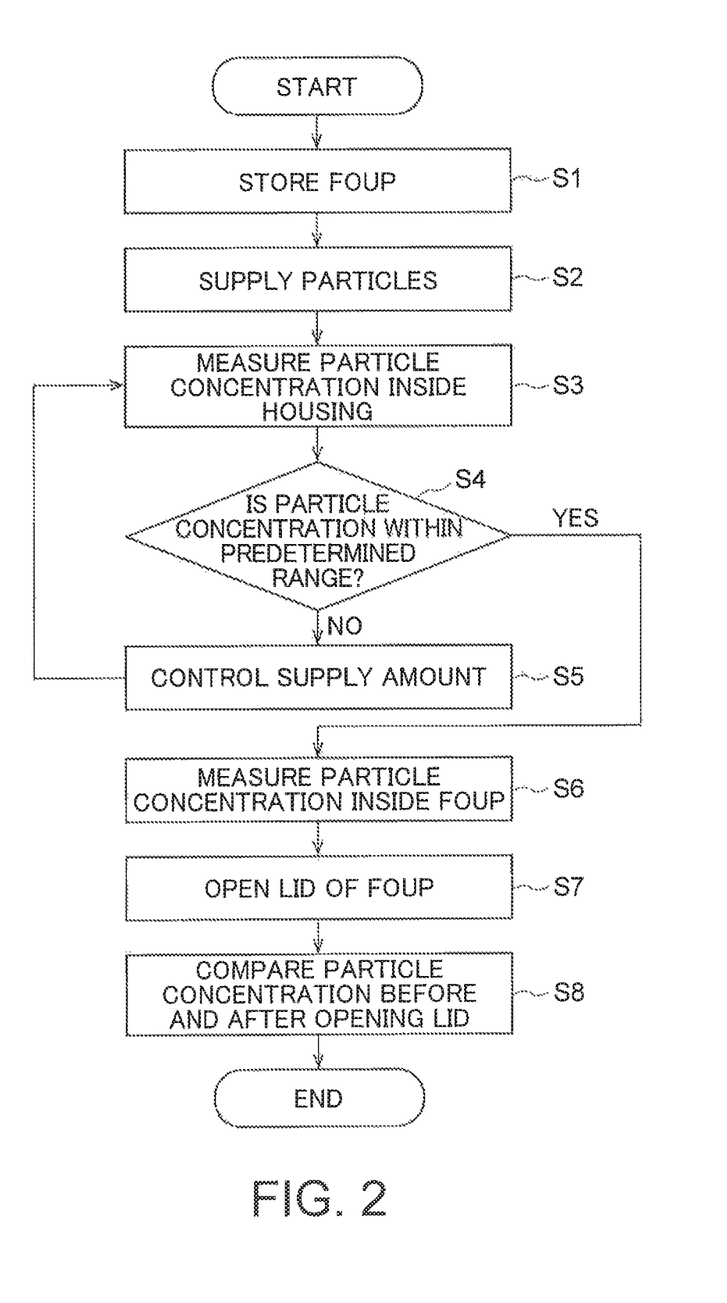
FIG. 2 is a flowchart illustrating a particle supply method according to the first embodiment.

Next, a particle supply method according to the present embodiment will be explained with reference to FIG. 2. FIG. 2 is a flowchart illustrating the particle supply method according to the present embodiment.

In step S1, the FOUP 5 serving as an evaluation target is stored in the housing 1 and disposed at a predetermined position of the table 64. At this time, the front surface of the housing 1 comes in contact with the load port 63. With this configuration, the sealed space covering the FOUP 5 is formed.

In step S2, the particle supplier 2 starts to supply the particles P to the sealed space inside the housing 1. At this time, it is preferable that the inside of the housing 1 be cleaned before starting the supply of the particles P. The inside of the housing 1 can be cleaned, for example, by discharging air from the inside of the housing 1 and supplying cleaned air to the inside of the housing 1. The air discharge from the inside of the housing 1 can be performed by the particle concentration measurer 3. Further, the air supply to the inside of the housing 1 can be performed by supplying air inside the conveyance chamber 62. Moreover, the particle supply device may be provided with a cleaning device which cleans the inside of the housing 1.

In step S3, the particle concentration measurer 3 starts to measure the particle concentration inside the housing 1. The particle concentration measurer 3 sucks the air inside the housing 1 and measures the particle concentration by counting the number of particles included in the sucked air. The measurement of the particle concentration may be started simultaneously with the supply of the particles P.

In step S4, the particle concentration controller 4 acquires the particle concentration inside the housing 1 measured by the particle concentration measurer 3 and determines whether the particle concentration inside the housing 1 is within the predetermined range. If the particle concentration is outside the predetermined range (NO in step S4), the process proceeds to step S5. If the particle concentration is within the predetermined range (YES in step S4), the process proceeds to step S6.

In step S5, the particle concentration controller 4 controls the supply amount of the particles P from the particle supplier 2 in such a manner that the particle concentration inside the housing 1 is within the predetermined range. Hereinafter, steps S3 to S5 are repeated until the particle concentration is within the predetermined range.

In step S6, the particle concentration measurer 3 starts to measure the particle concentration inside the FOUP 5. The particle concentration inside the FOUP 5 can be measured, for example, by the PC provided at the FOUP 5. It should be noted that the measurement of the particle concentration inside the FOUP 5 can be started at arbitrary timing until step S6.

In step S7, the lid 52 of the FOUP 5 and the lid 65 of the EFEM 6 are opened. As described above, when the lid 52 of the FOUP 5 is opened, outside air intrudes into the FOUP S through the gap G. At this time, since the sealed space by the housing 1 is formed around the FOUP 5, the air inside the housing 1 whose particle concentration or particle diameter is controlled intrudes into the FOUP 5.

In step S8, the particle concentration inside the FOUP 5 before opening the lid 52 and the particle concentration inside the FOUP 5 after opening the lid 52 are compared.

With this configuration, the amount of particles P intruded from the gap G by opening the lid 52 can be evaluated.

As described above, according to the particle supply device and the particle supply method of the present embodiment, the material, the particle diameter, the particle concentration, and the like of the particles P inside the housing 1 can be controlled. Therefore, by using the particle supply device and the particle supply method of the present embodiment, dust intrusion evaluation can be performed in a state in which the environmental conditions are controlled. With this configuration, for example, the environmental conditions at the time of the dust intrusion evaluation are made constant, and highly reliable evaluation can be performed, Further, it is possible to perform the evaluation on the plurality of load ports 63 under the same environmental conditions or to perform the evaluation under the same environmental conditions as those in the clean room utilized by the FOUP 5.

Figure 3:
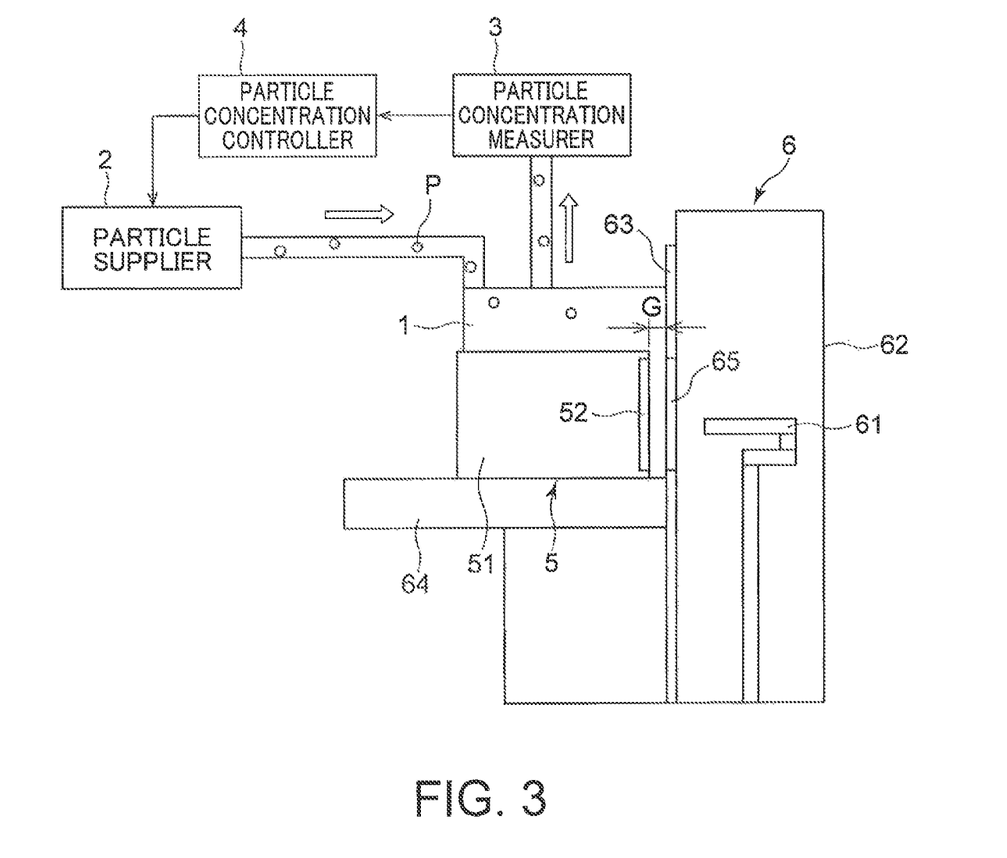
FIG. 3 is a schematic configuration diagram illustrating another example of the particle supply device according to the first embodiment.

It should be noted that in the present embodiment, the sealed space formed by the housing 1 may be formed so as to cover the gap G between the front surface of the FOUP 5 and the load port 63. Because of this, as illustrated in FIG. 3, the housing 1 may be configured to store a portion of the FOUP 5 as long as the sealed space covering the gap G can be formed.

Figure 4:
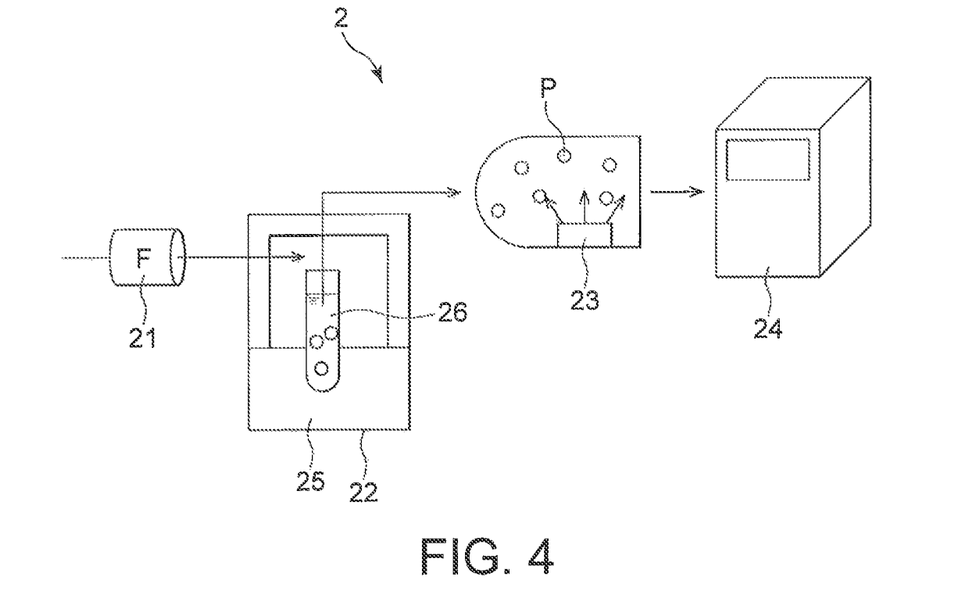
FIG. 4 is a schematic configuration diagram illustrating a concrete example of a particle supplier.

Here, FIG. 4 is a schematic configuration diagram illustrating a concrete example of the particle supplier 2 according to the present embodiment. The particle supplier 2 in FIG. 4 includes an inlet 21, a particle generator 22, a charge neutralizer 23, and a particle diameter filter 24.

The inlet 21 includes a particulate filter. The inlet 21 cleans the sucked air with the particulate filter and supplies the cleaned air to the particle generator 22. The inlet 21, for example, sucks air in the clean room or the conveyance chamber 62 and supplies the air to the particle generator 22.

The particle generator 22 generates the particles P. The particle generator 22 stores a suspension 25 including the particles P and sucks up the suspension 25 by a capillary tube 26. While the suspension 25 is sucked up by the capillary tube 26, the suspension 25 is vaporized and the particles P are generated. The charge neutralizer 23 charges the particles P generated by the particle generator 22 to a predetermined charge.

The particle diameter filter 24 sorts out the particles P charged by the charge neutralizer 23 based on the particle diameter. Specifically, the particle diameter filter 24 emits the particles P into an electric field. Since the particles P are charged, movement amounts in the electric field change corresponding to the particle diameter (mass). By taking out the particles P for every movement amount in the electric field, the particle diameter filter 24 can sort out the particles P based on the particle diameter. The particle diameter filter 24 sorts out the particles P with a predetermined particle diameter and supplies the particles P to the inside of the housing 1. With this configuration, the particles P having a uniform particle diameter can be supplied to the inside of the housing 1.

In a case where the particle supplier 2 is configured in this way, the particle concentration controller 4 can change the supply amount of the particles P from the particle supplier 2 and control the particle concentration inside the housing 1 by, for example, controlling an air supply amount from the inlet 21.

(Second Embodiment)

Figure 5:
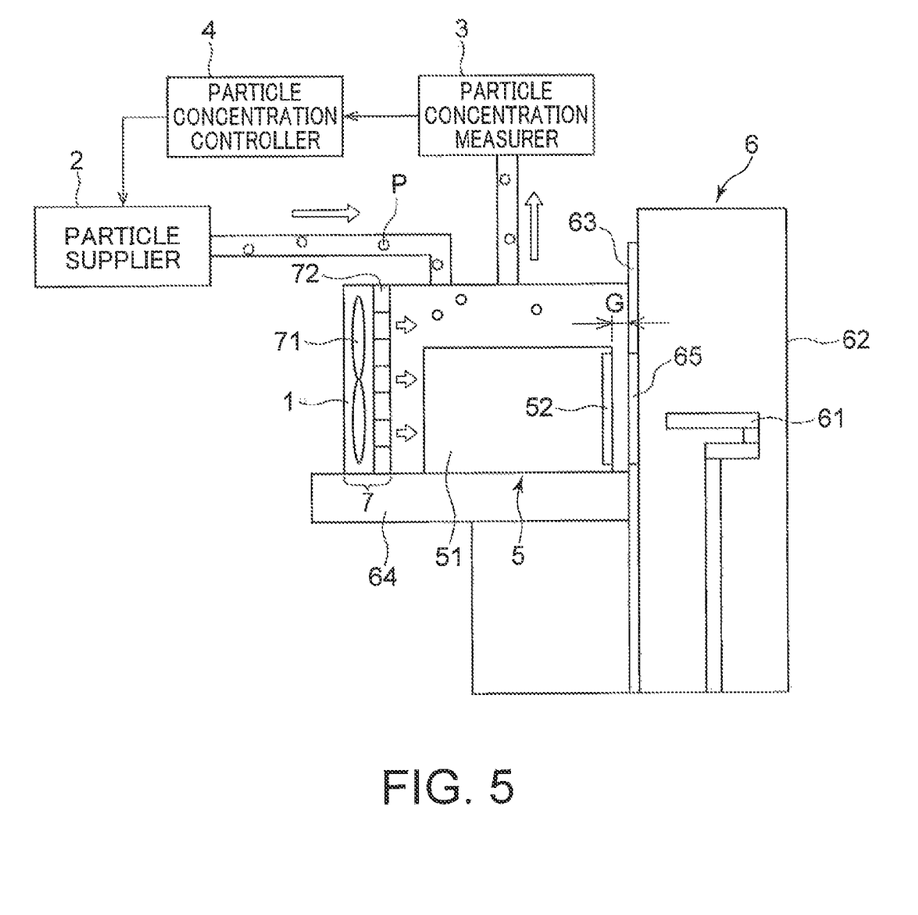
FIG. 5 is a schematic configuration diagram illustrating one example of a particle supply device according to a second embodiment.
Figure 6:
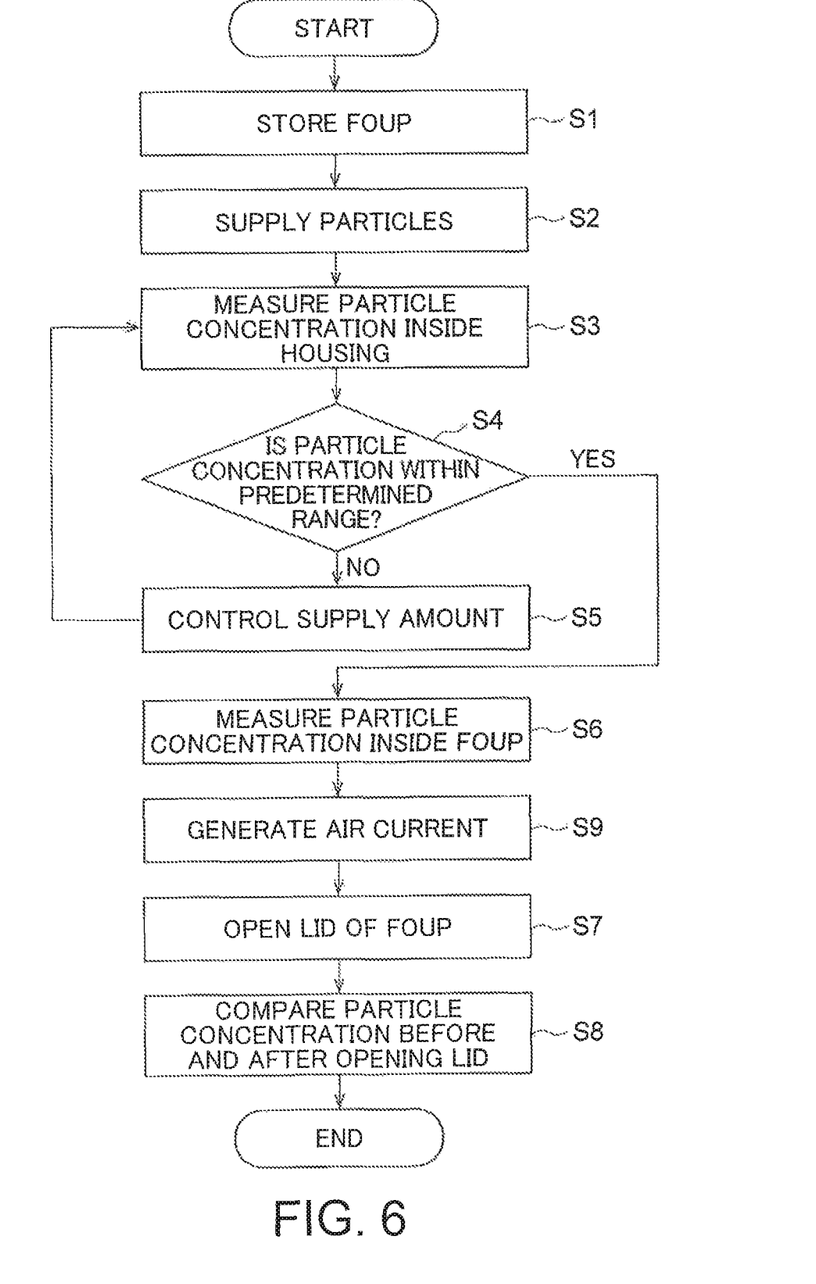
FIG. 6 is a flowchart illustrating one example of a particle supply method according to the second embodiment.

A particle supply device and a particle supply method according to a second embodiment will be explained with reference to FIGS. 5 and 6. First, the particle supply device according to the present embodiment will be explained with reference to FIG. 5. FIG. 5 is a schematic configuration diagram illustrating one example of the particle supply device according to the present embodiment. As illustrated in FIG. 5, this particle supply device further includes an air blower 7. The other configuration is the same as that of the first embodiment.

The air blower 7 is provided inside a housing 1 and generates an arbitrary air current inside the housing 1. The air blower 7 generates, for example, the air current simulating an air current in a clean room utilized by a FOUP 5. The air blower 7 includes a fan 71 and a louver 72.

The fan 71 generates an air current in a predetermined direction inside the housing 1. The position and the number of fans 71 to be arranged and the direction of the air current generated by the fan 71 can be designed arbitrarily. Further, a FFU may be provided instead of the fan 71.

The louver 72 adjusts the direction of the air current generated by the fan 71. With this configuration, the air current in the arbitrary direction can be generated inside the housing 1.

Next, the particle supply method according to the present embodiment will be explained with reference to FIG. 6. FIG. 6 is a flowchart illustrating the particle supply method according to the present embodiment. As illustrated in FIG. 6, this particle supply method further includes step S9 before step S7. The other process is the same as that of the first embodiment.

In step S9, the air blower 7 starts to blow air and generates the air current inside the housing 1. The arbitrary air current can be generated around the FOUP 5 by the air blower 7. This step S9 can be performed at arbitrary timing before step S7.

As described above, according to the particle supply device and the particle supply method of the present embodiment, the air current around the FOUP 5 can be controlled. For example, by reproducing an air current in the clean room utilized by the FOUP 5, the intrusion of dust when the FOUP 5 is actually utilized can be evaluated with a higher degree of accuracy.

(Third Embodiment)

Figure 7:
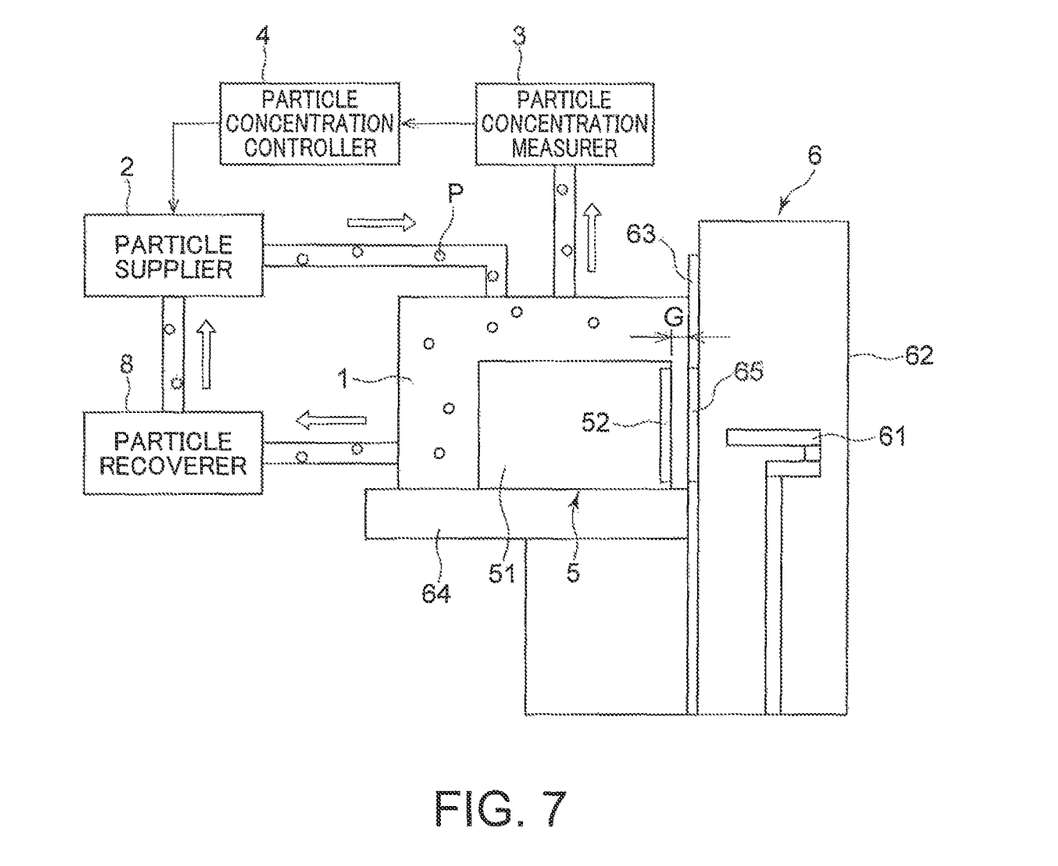
FIG. 7 is a schematic configuration diagram illustrating one example of a particle supply device according to a third embodiment.

A particle supply device and a particle supply method according to a third embodiment will be explained with reference to FIG. 7. Here, FIG. 7 is a schematic configuration diagram illustrating one example of the particle supply device according to the present embodiment. As illustrated in FIG. 7, this particle supply device further includes a particle recoverer 8. The other configuration is the same as that of the first embodiment. The particle itecoverer 8 sucks air inside a housing 1 and recovers particles P inside the housing 1. In FIG. 7, the particle recoverer 8 sucks air from a back surface of the housing 1. However, the particle recoverer 8 may suck the air from an upper surface or a side surface of the housing 1, or may suck the air from a plurality of positions of the housing 1. The particles P recovered by the particle recoverer 8 are fed to a particle supplier 2 and supplied again to the housing 1 by the particle supplier 2.

In the particle supply method according to the present embodiment, in step S2, the particle supplier 2 starts to supply the particles P, and the particle recoverer 8 starts to recover the particles P. The other process is the same as that of the first embodiment.

As described above, according to the particle supply device and the particle supply method of the present embodiment, since the particles P inside the housing 1 are recovered by the particle recoverer 8, the particles P inside the housing 1 can be reused. Further, excessive supply of the particles P to the inside of the housing 1 is prevented and the particle concentration inside the housing 1 can be easily controlled. Moreover, since the particles P recovered by the particle recoverer 8 can be reused, an amount of the particles P used is reduced and an evaluation cost can be suppressed.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A particle supply device comprising:
   a housing to seal a space between a substrate carry-out port provided in a FOUP and a substrate carry-in port provided at a load port of a substrate processing device;
   a particle supplier to supply particles to an inside of the housing; and
   a particle recoverer to recover the particles supplied to the inside of the housing.

2. The device according to claim 1, further comprising a particle concentration measurer to measure a particle concentration inside the housing.

3. The device according to claim 1, further comprising a particle concentration controller to control a supply amount of the particles from the particle supplier in such a manner that the particle concentration inside the housing becomes a predetermined value.

4. The device according to claim 3, wherein the predetermined value is an average value or a maximum value of the particle concentration in a space utilized by the FOUP.

5. The device according to claim 1, wherein the particles are standard particles having a uniform particle diameter.

6. The device according to claim 1, wherein the particles are PLS particles.

7. The device according to claim 1, wherein the housing has an opening part on a front surface and is disposed in such a manner that the opening part comes in contact with the load port.

8. The device according to claim 1, wherein the housing forms a sealed space including the FOUP.

9. The device according to claim 1, further comprising a cleaning device to clean the inside of the housing.

10. The device according to claim 1, further comprising a fan to generate an air current in a predetermined direction inside the housing.

* * * * *